United States Patent [19]

Lanham et al.

[11] 4,000,041

[45] Dec. 28, 1976

[54] *E. COLI* IDENTIFICATION BROTH

[75] Inventors: James W. Lanham, St. Louis; Ralph A. Wilkinson, Florissant; Leodis V. Woods, St. Louis, all of Mo.

[73] Assignee: McDonnell Douglas Corporation, St. Louis, Mo.

[22] Filed: May 3, 1976

[21] Appl. No.: 682,252

[52] U.S. Cl. .................... 195/100; 195/103.5 R; 195/102
[51] Int. Cl.$^2$ .................................. C12K 1/10
[58] Field of Search ........... 195/99, 100, 101, 102, 195/103, 103.5 R

[56] References Cited

OTHER PUBLICATIONS

Merck Index, 8th ed.; p. 290.

*Primary Examiner*—A. Louis Monacell
*Assistant Examiner*—Robert J. Warden
*Attorney, Agent, or Firm*—Gravely, Lieder & Woodruff

[57] ABSTRACT

A broth medium for the identification of *Escherichia coli*. The medium employs coumaric acid, preferably para-coumaric acid, to inhibit growth and metabolic activity of other gram negative microorganisms and thus eliminate false positive test results in a medium designed for *E. coli* organisms.

7 Claims, No Drawings

E. COLI IDENTIFICATION BROTH

BACKGROUND OF THE INVENTION

Escherichia coli (E. Coli) is a gram negative bacterium which occurs naturally in the intestinal tract of warm-blooded animals. The presence of this organism is a reliable indicator of fecal contamination. If E. coli bacterium is present in a given sample of material such as water, fecal matter, etc., it is also possible that Salmonella, Shigella, Vibrio, enteric viruses, and intestinal parasites are also present in the sample.

No process is presently known whereby the presence of E. coli can be reliably detected merely by growing the organism in or on a specific medium. current processes used to detect and identify this microorganism involve visual inspection of pure culture colonies, and a series of subsequent biochemical tests.

The present process involves the usual initial or preliminary steps of isolating individual bacteria known in microbiology. In such processes, agar containing added nutrients is a common support media employed in the culturing of microorganisms for the purpose of isolating and identifying individual bacteria. A method of isolating individual bacteria involves culturing microorganisms on agar plates. This process involves streaking the surface of an agar plate (a Petri-dish containing agar fortified with nutrients) with a sample containing different microorganisms. The individual organisms are deposited along the track of the streak. Thereafter the agar plate is incubated at selected temperatures for a period of time. The individual organisms grow in colonies along the track of the streak and may be further isolated by subculturing, i.e., taking a sample from a particular colony which is partially contaminated and repeating the process with another agar plate.

In the present invention, after a pure culture is isolated, it is placed in the medium of this invention, and if it is E. coli, a change occurs in the broth which identifies the organism to the observer as E. coli.

We have discovered a medium which will selectively identify E. coli. This medium will yield relatively few positive results in the presence of Klebsiella or Enterobacter. The essential ingredient of this medium is coumaric acid, preferably para-coumaric acid. The ortho - and meta - forms of coumaric acid also are effective, but are less reliable whereas the para form effectively inhibits nearly all fecal coliform organisms except E. coli.

SUMMARY OF THE INVENTION

This invention involves a broth medium for the identification of cultures of E. coli.

The medium contains coumaric acid, preferably para-coumaric acid, a source of carbon, a source of nitrogen, a gram positive inhibitor and a biological pH indicator which registers the acid produced by E. coli.

The coumaric acid functions to inhibit fecal coliforms, such as Klebsiella and Enterobacter, which would normally tend to yield false positive test results in the absence of coumaric acid.

DETAILED DESCRIPTION

The identification broth of the present invention contains from 0.5 to 4.0% (w/w) of a carbon source which is assimilated by E. coli, about 0.01 to about 0.1% (w/w) of an indicator which indicates the positive growth and metabolism of E. coli organism by turning color in response to production of an acid by metabolism of the E. coli organism in the medium, 0.15 to 1.50% (w/w) surfactant or other inhibitor of gram positive organisms, 0.3 to 1.5% (w/w) nitrogen source, and about 0.1 to about 1.0% (w/w) coumaric acid to inhibit the growth of other coliform-like gram negative organisms which often give positive results in tests for E. coli by current methods.

The major carbon source is lactose. The purpose of the lactose is to provide a source of energy for growth and metabolism of the coliform organisms. These organisms, including E. coli, ferment lactose and produce acids, so that the use of lactose is important to this medium. Utilization of lactose by E. coli is known in the art.

Suitable nitrogen sources are proteins or peptones, such as Gelysate, Trypticase, Phytone, and Polypeptone. These materials provide a source of nitrogen required for complete metabolic activity of the organism.

Suitable surfactants are Bile Salts Mixture from BBL or Bile Salts No. 3 from Oxoid, and other similar products made by other manufacturers. The purpose of the bile salts is to inhibit growth of gram positive organisms. Additional compounds which may be added to inhibit growth of gram positive bacteria are deoxycholic acid (0.1 – 0.9%); cholic acid (0.1 – 1.0%); taurodeoxycholic acid (0.05 – 0.25%); lithocholic acid (0.005 –0.045%); taurocholic acid (0.1 – 0.3%); Brilliant Green (0.001 – 0.008%); crystal violet (0.0001 – 0.00005%); and Tergitol 7 (0.005 – 0.1%). Gram positive organisms are, as a class, susceptible to surfactant-like materials.

A suitable biological pH indicator is reduced or decolorized aniline blue. The aniline blue is described in detail in co-pending application of Aldrich and Meyer filed on even date herewith entitled "Sensitive pH Indicator". The aniline blue measures change of pH toward acid and turns a blue color as the pH moves toward acid.

The essence of this invention lies in the action of the chemical inhibitor coumaric acid. This inhibitor acts to selectively inhibit the metabolic activity of Klebsiella and Enterobacter species without appreciably affecting the metabolic activity of E. coli.

Both meta-coumaric acid and ortho-coumaric acid can be used in this invention. However, para-coumaric acid is much more effective than either the meta or ortho species.

PREPARATION

The following method is used to prepare 100 ml of the broth:

0.50 gm of para-coumaric acid is added to 80 ml of distilled water containing 0.13 gm sodium hydroxide. The solution is stirred until the acid dissolves. 2.0 gm of lactose and 0.50 gm of Gelysate are then added to the solution and dissolved. The pH of the resulting solution is adjusted to 7.5. Lactose should be added subsequent to the dissolution of coumaric acid. Failure to perform the steps in the prescribed order may result in hydrolysis of the lactose. 0.30 gm Bile Salts Mixture is added and dissolved by stirring. Then 0.05% reduced Aniline Blue is added. The volume is then brought up to 100 ml with distilled water, the pH readjusted to 7.4 – 7.5, and the broth is filter sterilized.

OPERATION

Two to four ml of the detection broth are placed in a 16 mm tube. A specimen from an agar plate is placed in the tube. After incubation for 16–18 hours at 35°C, if the color of the indicator chages from colorless to blue, the presence of E. coli organism is detected. If the color of the indicator does not change, E. coli was not present in the sample.

Table I shows the results of tests on various microorganisms with the identification broth of the present invention.

TABLE I

| Organisms Tested | Number of Strains | Reaction in E. coli broth | % Correlation |
|---|---|---|---|
| E. coli | 343 | 329 Positive | 95.9 |
| K. pneumoniae | 58 | 2 Positive | 96.5 |
| E. cloacae | 20 | 2 Positive | 90.0 |
| E. agglomorans | 21 | 0 Positive | 100.0 |
| Misc. Kleb/Enteros | 89 | 4 Positive | 95.5 |
| Misc. Gm Negatives | 27 | 0 Positive | 100.0 |
| Misc. Gm Positives | 14 | 0 Positive | 100.0 |

Only 4.1% false negative results were obtained and only 2.3% false positives. All of the false positives occurred with water-borne Klebsiella/Enterobacter strains obtained from sewage treatment plant effluents.

It has been determined that water-borne E. coli damaged by the chlorine treatment experience some difficulty in initial metabolic activity in this broth on initial isolation.

Once obtained in pure culture, however, there are no detectable differences between water borne and clinical isolates of E. coli.

What is claimed is:

1. A composition for selectively identifying E. coli comprising:
   a. a source of nutrients,
   b. an indicator to visually show the presence of E. coli organism, and
   c. coumaric acid as an inhibitor to inhibit the growth of other coliform-like organisms which normally give positive results in tests for E. coli.

2. The composition of claim 1 wherein the inhibitor is para-coumaric acid.

3. The composition of claim 1 wherein the inhibitor is 0.1 to 1.0% para-coumaric acid.

4. The composition of claim 1 wherein the indicator is reduced aniline blue which turns blue on production of acid by the E. coli.

5. The composition of claim 1 comprising:
   a. from about 0.1 to about 1.0% para-coumaric acid,
   b. from about 0.5 to about 4.0% carbon source,
   c. from about 0.3 to about 1.5% nitrogen source,
   d. from about 0.15 to about 1.5% gram positive organism inhibitor,
   e. from about 0.01 to about 0.1% biological pH indicator, and
   f. distilled water to 100%.

6. The composition of claim 5 wherein the carbon source is lactose.

7. The composition of claim 1 comprising:
   a. about 0.5% para-coumaric acid,
   b. about 2.0% lactose as a carbon source,
   c. about 0.5% Gelysate,
   d. about 0.3% surfactant as a gram positive organism inhibitor,
   e. about 0.05% reduced Aniline Blue as a pH indicator, and
   f. distilled water to 100%.

* * * * *